(12) United States Patent
Ohzawa

(10) Patent No.: US 6,965,663 B2
(45) Date of Patent: Nov. 15, 2005

(54) X-RAY ANALYSIS APPARATUS AND METHOD

(75) Inventor: Sumito Ohzawa, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 104 days.

(21) Appl. No.: 10/396,847

(22) Filed: Mar. 25, 2003

(65) Prior Publication Data

US 2003/0215060 A1 Nov. 20, 2003

(30) Foreign Application Priority Data

Mar. 27, 2002 (JP) .............................. 2002-089305
Aug. 30, 2002 (JP) .............................. 2002-253699
Sep. 3, 2002 (JP) .............................. 2002-257453

(51) Int. Cl.[7] ......................................... G01N 23/223
(52) U.S. Cl. .................... 378/44; 378/145; 250/505.1
(58) Field of Search .............................. 378/44, 45, 46, 378/48, 49, 50, 145; 250/505.1

(56) References Cited

U.S. PATENT DOCUMENTS

| 4,461,017 A | 7/1984 | Koga et al. ................... 378/44 |
| 4,686,631 A * | 8/1987 | Ruud ........................... 702/42 |
| 5,412,705 A * | 5/1995 | Snoeren et al. ............. 378/98.3 |
| 5,740,223 A * | 4/1998 | Ozawa et al. ................ 378/161 |
| 5,896,438 A * | 4/1999 | Miyake et al. ................ 378/34 |

FOREIGN PATENT DOCUMENTS

| JP | 60-144646 | | 7/1985 | |
| JP | 60-253956 | * | 12/1985 | ........ G01N 23/223 |
| JP | 60253956 A | * | 12/1985 | ........ G01N 23/223 |

* cited by examiner

Primary Examiner—Edward J. Glick
Assistant Examiner—Courtney Thomas

(57) ABSTRACT

This invention provides an X-ray analysis apparatus and method capable of simply and accurately determining the position of analysis in a sample from an optical image of it without lowering the sensitivity and/or the spatial resolution in light element analysis. The X-ray analysis apparatus of the present invention irradiates a sample with X-rays narrowed down by means of an X-ray guide member from above the sample in which said sample is directly irradiated with X-rays from said X-ray guide member and an optical image of said sample is obtained in the direction coaxial with said X-ray guide member.

24 Claims, 6 Drawing Sheets

RELATED ART Fig. 6
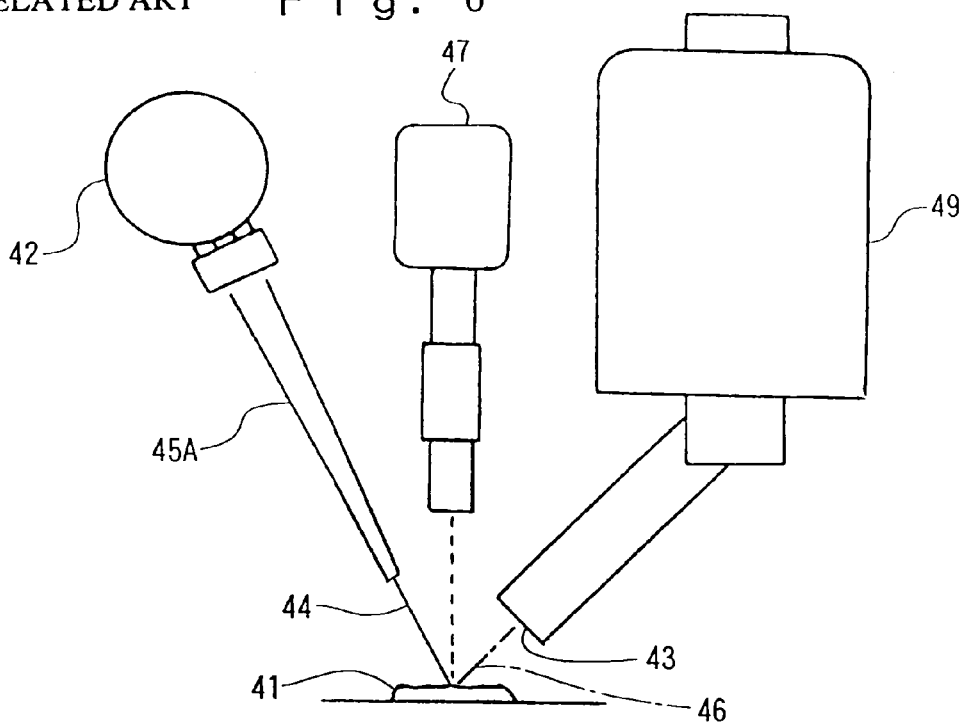
RELATED ART Fig. 7
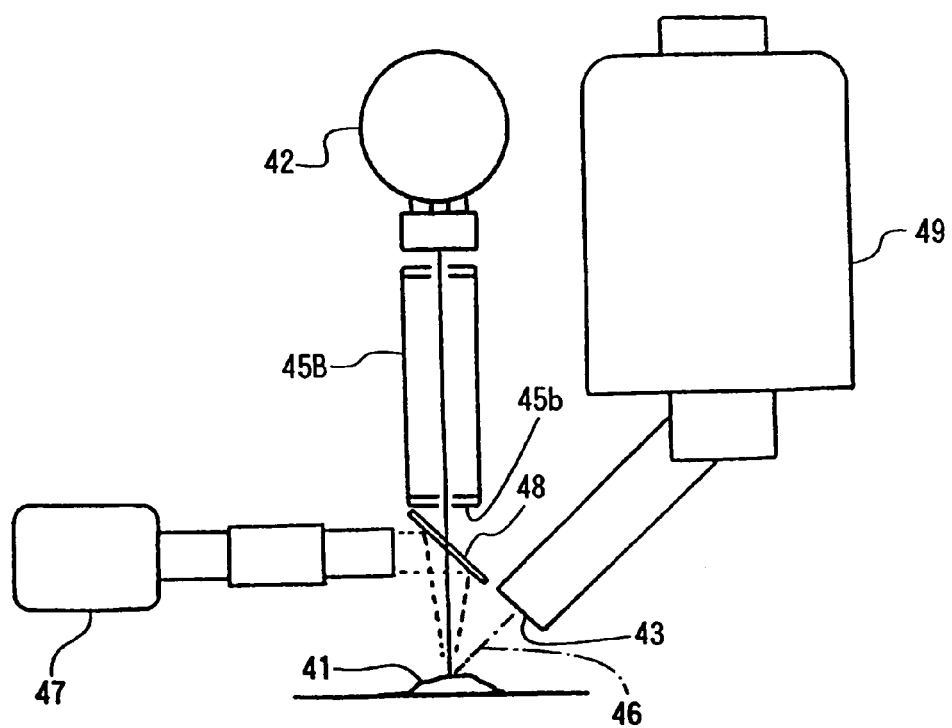

X-RAY ANALYSIS APPARATUS AND METHOD

FIELD OF INVENTION

The present invention relates to an X-ray analysis apparatus and method used for examining samples. More particularly, the invention relates to a method and apparatus for analyzing the kind, amount and distribution state of elements contained in a sample.

BACKGROUND OF THE INVENTION

An X-ray analysis apparatus irradiates a sample mounted on a sample stage with primary X-rays, detects secondary X-rays such as fluorescent X-rays, scattering X-rays and the like generated at that time by means of an X-ray detector, processes properly the detected output, and thereby makes it possible to analyze constituent elements of the sample or its internal structure.

Recently a demand for analyzing in more detail a microscopic part of a sample, using the X-ray analysis apparatus as described above, has been increased. To perform this more detailed analysis, a microscopic part of the sample is irradiated with X-rays narrowed down by means of an X-ray guide member such as an X-ray guide tube and the like. In this case it is desirable to observe what position of the sample is irradiated with the narrow-diameter X-ray beam by means of an observing means such as a CCD camera and the like, and display the observed image on the display screen of a display device attached to an arithmetic and control device such as a personal computer and the like for controlling the whole apparatus.

Exemplary conventional X-ray analysis apparatus are described in Japanese Patent Laid-Open Publication No. Hei 4-175648 and Japanese Patent Laid-Open Publication No. Hei 6-288941. FIG. 6 shows schematically an X-ray analysis apparatus disclosed in Japanese Patent Laid-Open Publication No. Hei 4-175648, and in this X-ray analysis apparatus there are provided an X-ray tube 42 and an X-ray detector 43 so as to be opposite to each other obliquely above a sample 41, so that characteristic X-rays (fluorescent X-rays for example) 46 generated when the sample 41 is irradiated with X-rays (primary X-rays) 44 which have been emitted from the X-ray tube 42 and narrowed down by an X-ray guide member 45A are detected by means of the X-ray detector 43, and a CCD camera 47 as a sample observing means is provided directly above the sample 41 so as to observe an optical image (visible light image) of the sample 41 in a different direction (inclined direction) from the direction of irradiation of the X-rays 44 (the X-ray irradiation axis).

FIG. 7 shows schematically an X-ray analysis apparatus disclosed in Japanese Patent Laid-Open Publication No. Hei 6-288941 and this X-ray analysis apparatus provides an X-ray tube 42 and an X-ray guide member 45B, such as a collimator, directly above a sample 41, further provides a half mirror 48 made of beryllium leaf being low in X-ray absorptivity below the X-ray guide member 45B so that it makes an angle of 45° with the direction of X-ray irradiation, provides a CCD camera 47 at the reflecting surface side of it, and thereby makes it possible to observe an optical image (visible light image) of the sample 41 coaxially with the axis of X-ray irradiation. In FIGS. 6 and 7, number 49 refers to a tank containing a cooling medium for cooling the X-ray detector 43.

As shown in FIG. 6 described above, however, in an X-ray analysis apparatus made to observe an optical image at an angle with the direction of X-ray irradiation, when the height of a sample is changed, a difference (discrepancy) arises between the position of observing an optical image and the position of X-ray irradiation in the sample 41, and if the surface of the sample is uneven it is not possible to exactly determine the position of analysis. And even in case that the surface of a sample is not uneven, since the position of analysis is determined depending on the accuracy of determining the height of the sample 41, a mechanism for accurately setting the height is required, requiring thereby an apparatus that is complex in structure.

On the other hand, in the X-ray analysis apparatus shown in FIG. 7, since an optical image (visible light image) of a sample 41 is observed coaxially with the axis of X-ray irradiation, a disadvantage as described above in connection with the apparatus illustrated in FIG. 6 does not occur, but since the sample 41 is irradiated with X-rays 44 through the half mirror 48, even in case of using a material being low in X-ray absorptivity like beryllium leaf, at least some of the X-rays 44 are absorbed. Particularly, the lower the low-energy X-rays effective for exciting light elements are in energy, the more likely the X-rays are to be absorbed; it is not possible to avoid the lowering of analysis sensitivity in light element analysis. And it is unavoidable that the distance between the X-ray output end (the lower end 45b of the X-ray guide member 45B in this example) and the sample 41 is made larger by arranging the half mirror 48, and thereby the spatial resolution of the apparatus is lowered.

The present invention addresses the above-mentioned deficiencies, and an object of the invention is to provide an X-ray analysis apparatus and method being capable of simply and accurately determining the position of analysis in a sample from an optical image of it without lowering the sensitivity and the spatial resolution in light element analysis.

SUMMARY OF THE INVENTION

In order to attain the above-mentioned object, the present invention forms an X-ray analysis apparatus made to irradiate a sample with X-rays narrowed down by means of an X-ray guide member from above the sample in which said sample is directly irradiated with X-rays from said X-ray guide member and an optical image of said sample is obtained in the direction coaxial with said X-ray guide member.

Using the above-described apparatus, it is possible to obtain an optical image of a sample coaxially with the axis of irradiating the sample with X-rays and perform at the same time the irradiation of the sample with X-rays and the confirmation of an optical image (visible light image) of the sample to be irradiated with X-rays in X-ray analysis of the sample. Therefore, it is possible to confirm, for example, visually the state (situation) of the sample while irradiating the sample with X-rays, and accurately determine the position of analysis even in case that the surface of the sample is uneven. Since a sample is directly irradiated with X-rays for X-ray analysis, the X-rays are not absorbed by a mirror and the analysis sensitivity is not lowered even in light element analysis. Further, since it is possible to make the X-ray output end of an X-ray guide member as close as possible to a sample, it is also possible to prevent the spatial resolution from lowering.

More concretely, the present invention provides an X-ray analysis apparatus for irradiating a sample with X-rays narrowed down by means of an X-ray guide member from above the sample, being provided with a mirror having an X-ray guide member through-insertion portion above said sample so that the reflecting surface of it faces the sample side and makes a specified angle with the direction of irradiating X-rays, making the lower end side of said X-ray guide member be inserted into said X-ray guide member through-insertion portion, and being provided with a collective lens having a large numerical aperture (e.g., greater than about 0.1) for converging the light reflected by said reflecting surface in a direction making a specified angle with said reflecting surface on a sample observing means.

Hereupon, a through hole may be formed in a reflecting surface as an X-ray guide member through-insertion portion generated in the reflecting surface of a mirror so as to make the lower end side of the X-ray guide member be inserted through it. Alternatively, a depression shallow (small) in cut or a depression deep (large) in cut may be provided in the reflecting surface, and it is acceptable also that the mirror is formed out of plural (two for example) mirror members and a specified gap is formed between these mirror members.

In accordance with one embodiment of the invention, the X-ray analysis apparatus includes a paraboloid mirror, having its focus at the position of a sample, that is provided around the X-ray guide member between the mirror and the sample. In such a case, it is possible to optionally select the height of a mirror relative to a sample.

In an X-ray analysis apparatus made to irradiate a sample with X-rays narrowed down by means of an X-ray guide member from above the sample, it is acceptable also to irradiate directly said sample with X-rays from said X-ray guide member and provide an optical fiber along said X-ray guide member. In such a case, a mirror for reflecting visible light and a collective lens are made unnecessary and thereby the structure is more simplified.

Further, in an X-ray analysis apparatus made to irradiate a sample with X-rays narrowed down by means of an X-ray guide member from above the sample, it is also acceptable to provide a concave mirror having an X-ray guide member through-insertion portion in its reflecting surface above said sample so that the reflecting surface of it faces the sample side, make the lower end of said X-ray guide member be inserted through into said X-ray guide member through-insertion portion, and provide a sample observing means in which the light reflected by said reflecting surface enters at the focus position of said reflecting surface. In such a case, a collective lens is made unnecessary.

In an X-ray analysis method made to irradiate a sample with X-rays narrowed down by means of an X-ray guide member from above the sample, it is also acceptable to irradiate directly said sample with X-rays from said X-ray guide member and obtain an optical image of said sample in a direction coaxial with said X-ray guide member. The action and effect of such an X-ray analysis method are the same as those of the X-ray analysis apparatus described above, in which the sample is directly irradiated from an X-ray guide member and an image of said sample is obtained in a direction co-axial with said X-ray guide member.

BRIEF DESCRIPTION OF THE DRAWINGS

FIG. 6 is a diagram for illustrating a conventional X-ray analysis apparatus; and FIG. 7 is a diagram for illustrating another conventional X-ray analysis apparatus.

DETAILED DESCRIPTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein.

Figure 1:
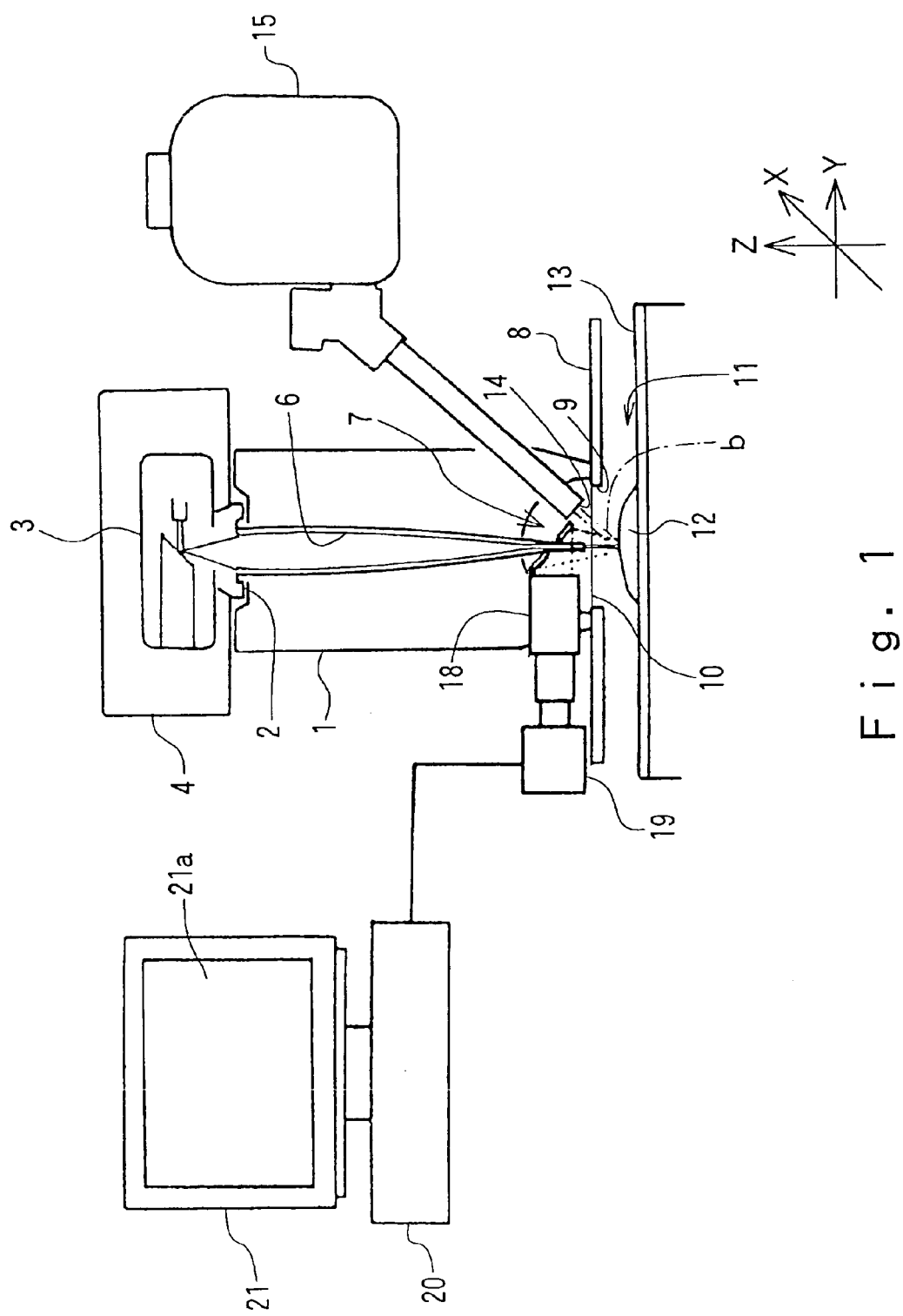
FIG. 1 is a diagram showing schematically an example of a main portion of an analysis part of an X-ray analysis apparatus of the present invention.
Figure 2:
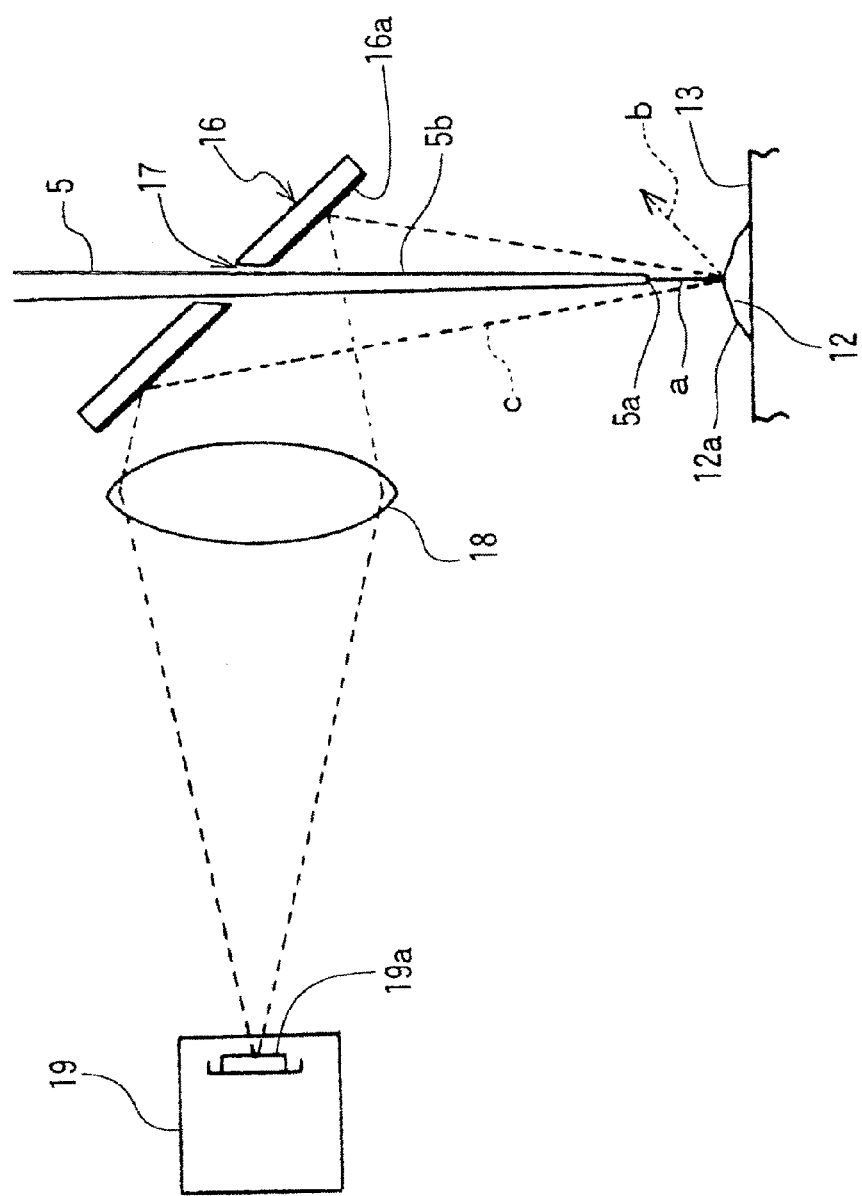
FIG. 2 is a diagram showing schematically an optical portion of said analysis part.

Details of the present invention are described with reference to the drawings in the following. FIGS. 1 and 2 show an embodiment of the present invention. FIG. 1 shows schematically an example of a main composition of an analysis part of an X-ray analysis apparatus of the present invention, and FIG. 2 is a diagram showing schematically an optical portion of said analysis part. In these figures, number 1 refers to a main body block of an X-ray analysis apparatus, above which there is provided an X-ray generator 4 containing an X-ray tube 3, a power source part (not illustrated) through a seal portion 2. The main body block 1 has a through-insertion hole 6 for allowing an X-ray guide tube 5 to be inserted as an X-ray guide member for guiding a primary X-ray beam emitted by the X-ray generator 4 as narrowing it down into a narrow beam diameter (about 10 to 100 $\mu$m in diameter) and irradiating a sample 12 (described later) with this narrow primary X-ray beam a, and a lower space 7 communicating with this through-insertion hole 6. The X-ray guide tube 5 is made gradually narrower from the top end to the lower end 5a, for example.

Reference number 8 corresponds to an X-ray shielding wall provided in the lower part of the main body block 1, more concretely, provided below the lower end 5a of the X-ray guide tube 5, and at a position in it corresponding to the X-ray output end (lower end) 5a of the lowest end of the X-ray guide tube 5 an opening 9 being proper in size is formed. Below this X-ray shielding wall 8, a space 11 being in the atmospheric pressure and air-tightly partitioned from the space 7 in the main body block 1 side by a thin diaphragm 10 made of a material transparent to X-rays, for example, polyethylene resin, is formed. The space 7 over the diaphragm 10 is referred to as an X-ray irradiation chamber, and the space 11 under the diaphragm 10 is referred to as a sample chamber 11.

In the sample chamber 11, a sample stage 13 having a sample 12 mounted on it is provided so that it can be moved straight respectively in the X direction (perpendicularly to the paper face), Y direction (horizontally in the paper face) and Z direction (vertically in the paper face) by a drive mechanism not illustrated. A door (not illustrated) used for inserting and taking out a sample 12 is provided at a proper position at the left side in the Y direction of sample chamber 11.

The inside of said X-ray irradiation chamber 7 is kept in a proper vacuum state together with the through-insertion hole 6, and has an X-ray output end 5a of the X-ray guide tube 5 and an X-ray detector 14 composed of a semiconductor detector for detecting fluorescent X-rays b (see FIG. 2) generated by irradiating a sample 12 with a primary X-ray beam a (see FIG. 2). In FIG. 1, number 15 corresponds to a tank containing a cooling medium for cooling the X-ray detector 14. The analysis components described above can be the same as the components of an analysis part in a conventional X-ray analysis apparatus of this kind. The present invention forms a means for observing a sample 12 and confirming an irradiated position of the sample 12 as described below.

Number 16 refers to a plane mirror provided in the X-ray irradiation chamber 7 above the sample 12, and its plan view is a rectangle for example and the plane mirror has a through hole 17 as a through-insertion part for having the X-ray guide tube 5 inserted as an X-ray guide member formed nearly in the middle of its reflecting surface 16a. Mirror 16 is provided so that its reflecting surface 16a faces the sample 12 side and makes an angle of about 45° with the direction of irradiating X-rays (the perpendicular direction in this case) and said through hole 17 is formed so as to be necessary and sufficient in size to have the lower end of the X-ray guide tube 5 perpendicularly inserted through it. Reflecting surface 16a is polish-finished so as to be capable of efficiently reflecting visible light. Although the lower end side of the X-ray guide tube 5 penetrates the through hole 17, it is preferable that the X-ray output end 5a of the lower end side is made as close as possible to the surface 12a of the sample 12. Further, in this case, it is preferable to form the outer circumferential surface 5b of the X-ray guide tube 5 projecting downward from the through hole 17 into a stray light preventing surface by applying an antireflection coating or the like to it. Although not illustrated in FIGS. 1 and 2, the apparatus is composed so that the sample 12 is irradiated with visible light.

Reference number 18 corresponds to a collective lens, which is provided so that the optical axis of it makes an angle of about 45° with the reflecting surface 16a of the mirror 16, and converges the visible light c which has emanated from the sample 12 and is reflected by the reflecting surface 16a of the periphery of the through hole 17 on the light receiving surface 19a of the CCD camera 19 as a sample observing means provided at a proper position in the light output side, and is composed of a lens of a high numerical aperture. The reason why a high-numerical aperture lens is used as the collective lens 18 is that it reflects the visible light c from the sample 12 by the mirror 16, particularly, by the reflecting surface 16a around (in the periphery of) the through hole 17 of the mirror 16, and ensures that a complete or substantially complete visible light image is obtained, rather than eclipsing the image due to using a small numerical aperture lens.

In FIG. 1, number 20 is an arithmetic and control unit such as a personal computer or the like provided with an image processing function, and has a function of controlling the whole apparatus, performing an arithmetic operation on the basis of output signals of the X-ray detector 14, the CCD camera 19 and the like, and image-displaying the result of arithmetic operation or the result of image processing on the display screen 21a of a display device 21.

In an X-ray analysis apparatus composed as described above, it is possible to obtain an optical image of a sample coaxially with the axis of irradiating the sample 12 with a primary X-ray beam a, and particularly perform at the same time the irradiation of the sample 12 with a primary X-ray beam a and the confirmation of an optical image of the sample 12 to be irradiated with X-rays in X-ray analysis of the sample 12. Therefore, it is possible to confirm the state (situation) of the sample 12 visually for example, while irradiating the sample 12 with a primary X-ray beam a, and determine the position of analysis in the sample 12 even when the sample is uneven in surface. And since a primary X-ray beam a to the sample 12 is irradiated to the sample 12 from a position as close as possible to the sample 12 by the X-ray guide tube 5 penetrating the though hole 17 of the mirror 16, even in case that a primary X- ray beam a used in a light element analysis is low in energy, absorption of the primary X-rays a by the mirror 16 is prevented and a light element analysis can be performed with high sensitivity. Furthermore, since the X-ray output end 5a of the X-ray guide tube 5 can be made as close as possible to the sample 12, the lowering of the spatial resolution can be prevented. Further, stray light of visible light c can be also prevented by forming the outer circumferential surface 5b of the X-ray guide tube 5 located below the mirror 16 into a stray light preventing surface through applying an antireflection coating or the like to it and thereby a clear optical image can be obtained.

Figure 3:
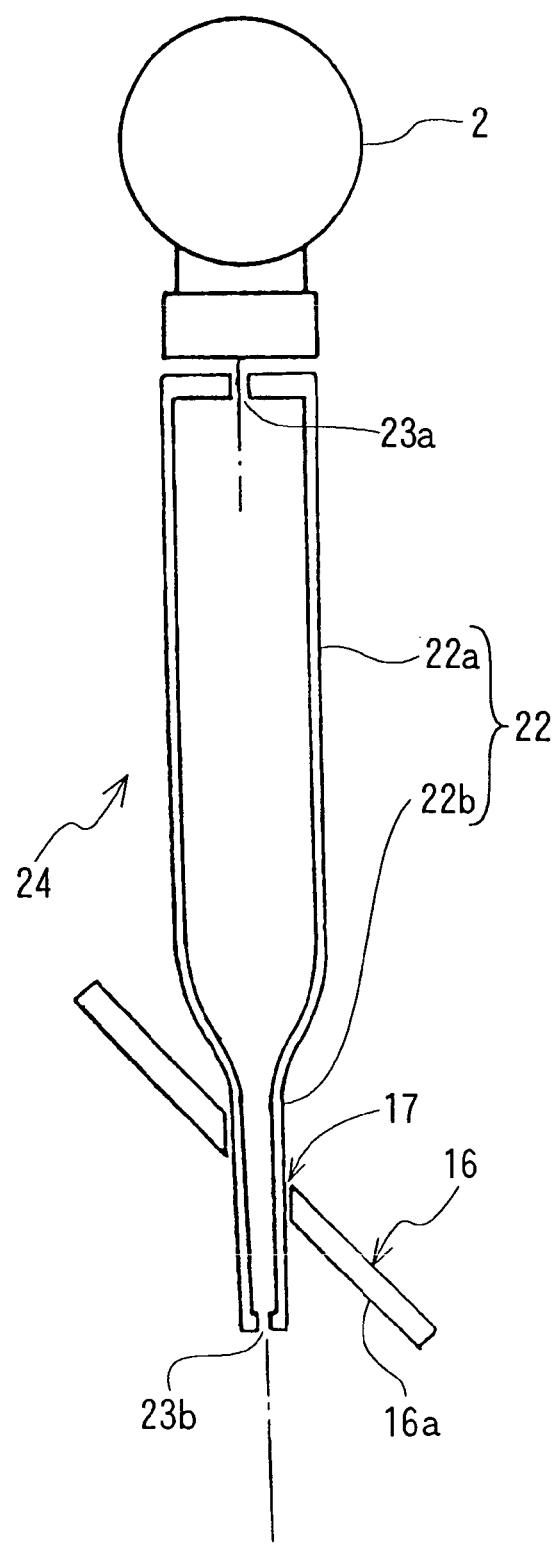
FIG. 3 is a diagram showing another embodiment of an X-ray guide member to be used in said analysis part.

Although the above-described embodiment uses an X-ray guide tube 5 as an X-ray guide member for guiding a primary X-ray beam a emitted by an X-ray generator 14 as narrowing it down into a narrow beam diameter, in place of this X-ray guide tube 5, as shown in FIG. 3, it is acceptable to use a collimator 24 of a double-pinhole type having a collimator cylinder 22 which is formed narrower in the lower end side 22b than the upper end side 22a and which has pinholes 23a and 23b respectively at the upper and lower ends and make the lower end side 22b be inserted through the through hole 17 of the mirror 16. In this case, it is preferable to form the outer circumferential surface of the lower end side 22b projecting downward from the through hole 17 into a stray light preventing surface.

Figure 4A:
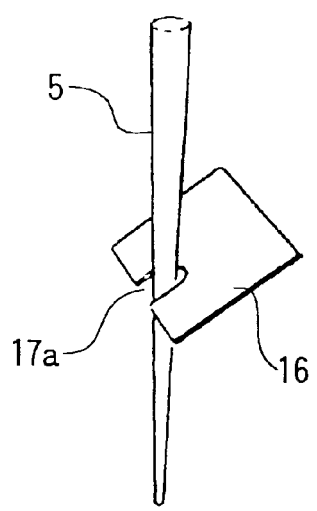
FIG. 4 is a diagram showing another embodiment of a mirror to be used in said analysis part.
Figure 4B:
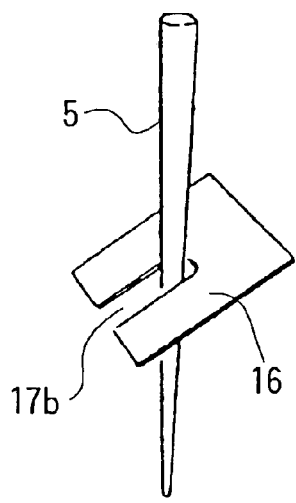
Figure 4C:
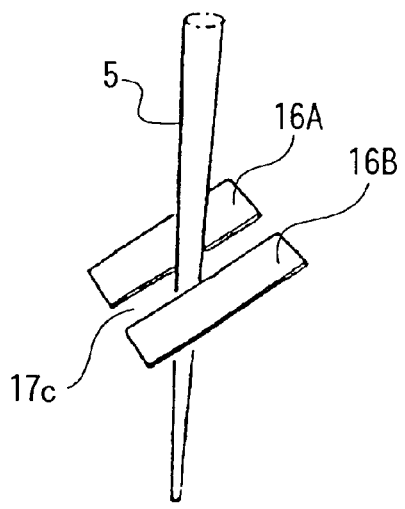

Although each of the above-mentioned embodiments forms the through hole 17 in the reflecting surface 16a of the mirror 16 and makes the lower end side of an X-ray guide member such as an X-ray guide tube 5, a collimator 24 and the like be inserted through into this through hole 17, various forms, as shown in FIGS. 4(A) to 4(C), are conceivable as a through-insertion portion having the lower end side of said X-ray guide member inserted into it without being limited to said through hole 17. That is to say, for example, in order to make the lower end side of an X-ray guide tube 5 be inserted through the mirror, it is acceptable also to form a shallow (small) cut 17a in a part of the reflecting surface 16 of a mirror 16 as shown in FIG. 4(A), form a deep (large) cut 17b as shown in FIG. 4(B), or form a mirror 16 by arranging plural (two for example) mirror members 16A and 16B in a row and then form a specified gap 17c between these mirror members 16A and 16B as shown in FIG. 4(C). The invention is not limited to these specific examples.

By way of particular example, in the case in which an X-ray guide tube 5 is made gradually narrower as going toward the lower end part and the outer diameter of the lower end part 5a is 0.5 mm and the outer diameter of a portion close to the through-insertion part is 3 mm and a mirror 16 is 20 mm×30 mm in size, the length of said cut 17a is about 4 mm. In case of alternately using plural X-ray guide tubes 5 or collimators 24, the alternating operation can be easily performed, for example, by using a through-insertion part 17a, 17b or 17c shown in FIGS. 4(A) to 4(C).

Although each of the above-mentioned embodiments uses a plane mirror 16 in order to obtain an optical image of a sample 12 coaxially with an X-ray guide member 5 or 24, it is possible to adopt various means as shown in FIG. 5 for example, in place of the plane mirror 16. That is to say, as shown in FIG. 5(A), in order to obtain an optical image of the sample 12, it is possible to arrange an optical fiber 25 to be used in, for example, an endoscope or the like along an X-ray guide tube 5 as an X-ray guide member so that the lower end of it is nearly equal in height to the lower end of the X-ray guide tube 5 and the upper end of it is connected to a CCD camera 19. In the case of using such an optical fiber, an arrangement as shown in FIG. 5(B) may be also adopted. That is to say, in FIG. 5(B), an optical fiber 26 obtained by bundling a plurality of optical fibers 26a each being in a single-fiber state is used in which these optical fibers 26a are provided near and around the lower end of the X-ray guide tube 5, as shown in a magnified view of FIG. 5(B). Any of the compositions shown in FIGS. 5(A) and 5(B) does not need a mirror 16 for reflecting visible light and/or a collective lens 18, and thereby makes the structure of the apparatus simpler.

Figure 5A:
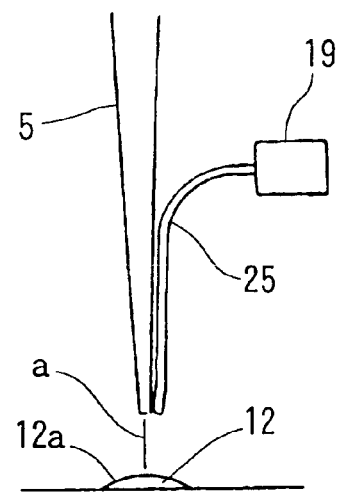
FIG. 5 is a diagram showing another embodiment for obtaining an optical image of a sample in said analysis part.
Figure 5B:
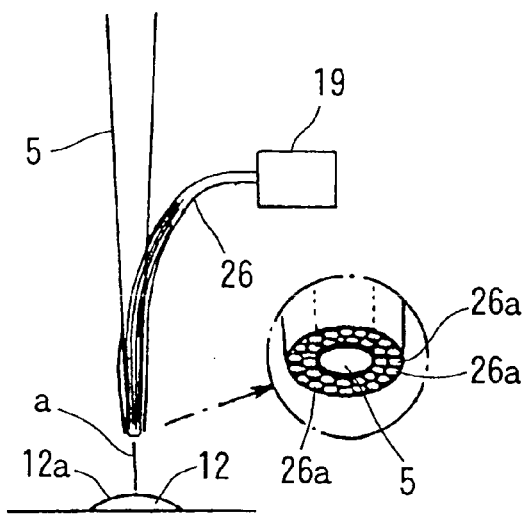
Figure 5C:
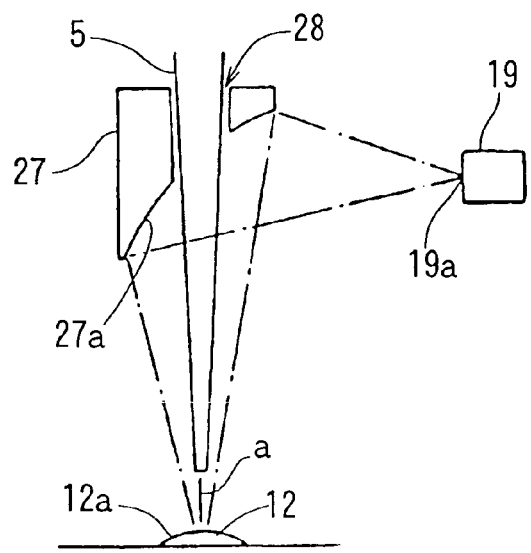

Furthermore, as shown in FIG. 5(C), it is acceptable also to provide a concave mirror (elliptical mirror) 27 whose reflecting surface 27a is concave (elliptical) as a mirror for collecting visible rays above a sample 12, form a through-insertion portion 28 for allowing an X-ray guide tube 5 to be inserted through the reflecting surface 27a of this mirror 27, make the lower end of the X-ray guide tube 5 be inserted through said through-insertion portion 28., and arrange a CCD camera 19 at the focus position of said reflecting surface 27a. According to this composition, since the mirror 27 serves as both a reflecting member and a collective member, a collective lens 18 is made unnecessary and thereby the apparatus is simplified.

Figure 5D:
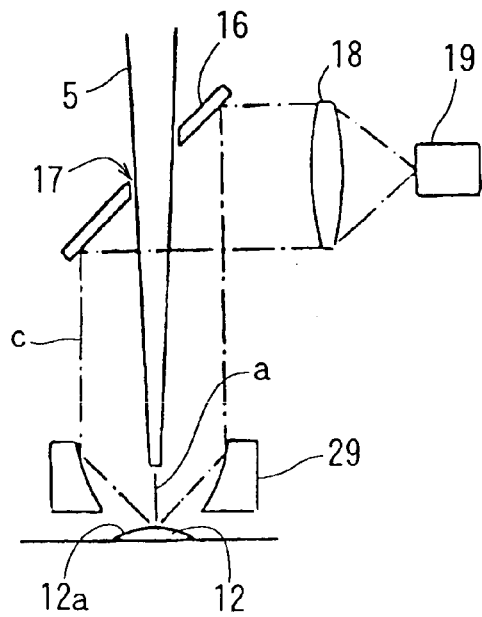

In an embodiment shown in FIG. 5(D), a paraboloidal mirror 29 is provided in the structure shown in FIG. 2, and in more detail said paraboloidal mirror 29 is provided around an X-ray guide tube 5 between a mirror 16 and a sample 12, and has the focus of it at the sample position; and according to this composition, since the reflected light c from the surface 12a of the sample 12 is incident on the mirror 16 as a light beam parallel with a vertical line, the height of the mirror 16 relative to the sample 12 can be optionally determined.

In the above-mentioned embodiments, a CCD camera is used as a sample observing means, but in place of this, another sample observing means such as an optical microscope and the like may be used and in this case it is enough to make the light such as visible light c and the like from the collective lens 18 form an optical image on the sample observing means. It is not always necessary to provide a thin diaphragm 10 under the main body block 1, and in case of omitting this, the X-ray output end 5a of an X-ray guide tube 5 can be made closer to the surface 12a of a sample 12.

As described above, in case of irradiating a sample with X-rays narrowed down by means of an X-ray guide member from above the sample, since the present invention irradiates directly said sample with X-rays from said X-ray guide member and obtains an optical image of the sample coaxially with said X-ray guide member, it is possible to obtain an optical image of the sample coaxially with the axis of irradiating the sample with the X-rays and perform at the same time the irradiation of a sample with X-rays and the confirmation of an optical image (visible image) of a sample to be irradiated with X-rays. Therefore, it is possible to confirm, for example, visually the state (situation) of a sample while irradiating the sample with X-rays and accurately determine the analysis position in a sample even when the surface of the sample is uneven. And since a sample is directly irradiated with X-rays for X-ray analysis, the X-rays are not absorbed by a mirror and the analysis sensitivity is not lowered, even in light element analysis. Furthermore, since it is possible to make the X-ray output end of an X-ray guide member as close as possible to a sample, it is possible also to prevent the spatial resolution from lowering.

According to an X-ray analysis apparatus and method of the present invention, therefore, it is possible to simply and accurately determine the position of analysis in a sample from an optical image without lowering the sensitivity and the spatial resolution in light element analysis and make high precision X-ray analysis.

Although the present invention is set forth herein in the context of the appended drawing figures, it should be appreciated that the invention is not limited to the specific form shown. For example, while various forms of mirror 16 and guide tube 5 have been illustrated, the invention is not so limited. Various other modifications, variations, and enhancements in the design and arrangement of the method and apparatus set forth herein, may be made without departing from the spirit and scope of the present invention as set forth in the appended claims.

What is claimed is:

1. An X-ray analysis apparatus comprising:
an X-ray guide member for narrowing and guiding X-rays from above a sample toward a surface of the sample such that said sample is directly irradiated with the X-rays along a first path; and
an optical reflective surface for receiving light reflected from said surface along a second path having a perimeter with an inwardly extending cut portion with the X-ray guide member extending through the cut portion and beyond the reflective surface,
wherein said first path and said second path are substantially coaxial.

2. An X-ray analysis apparatus comprising:
an X-ray guide member having a first end and a second end for irradiating a sample from above a surface of the sample along a path, wherein said second end is narrower than said first end;
a mirror comprising an X-ray guide member through-insertion portion and a reflecting surface, the mirror positioned above the sample such that the reflecting surface faces toward the sample at a specified angle with respect to the path, wherein a lower end of the X-ray guide member is positioned through said X-ray guide member through-insertion portion to protrude beyond said reflecting surface; and
a collective lens having a large numerical aperture for converging light reflected by said reflecting surface in a direction making a specified angle with said reflecting surface onto a sample observing means.

3. The X-ray analysis apparatus according to claim 2, wherein a parabolic mirror having its focus point near a position of the sample is provided proximate the X-ray guide member between said mirror and the sample.

4. An X-ray analysis apparatus according to claim 2 wherein said second end of the X-ray guide member extends through said X-ray guide member through-insertion portion to protrude from the reflecting surface face to a position adjacent a surface of the sample.

5. An X-ray analysis apparatus according to claim 4 wherein said through-insertion portion is one of a shallow cut portion extending inward from a perimeter of the mirror, a deep cut portion extending inward from a perimeter of the mirror and a gap extending through and dividing the mirror into a plurality of mirrors.

6. An X-ray analysis apparatus comprising:
   an X-ray guide member having a first end and a second end for irradiating a sample from above a surface of the sample along a path, wherein said second end is narrower than said first end;
   a concave mirror having an aperture formed therein for receiving a portion of the X-ray guide member and a reflecting surface located above the sample, such that the reflecting surface faces the sample, the X-ray guide member extends through and protrudes from said reflecting surface; and
   a sample observing means for receiving light reflected by and focused by said reflecting surface.

7. An X-ray analysis apparatus comprising:
   an X-ray guide member for transmitting X-rays to a sample;
   a reflective surface having a through-hole formed therein for receiving a portion of said X-ray guide member that extends through and protrudes from said reflective surface; and
   an optical light receiving apparatus for receiving optical light from said reflective surface.

8. The X-ray analysis apparatus of claim 7, further comprising a detector for detecting fluorescent X-rays emanating from the sample.

9. The X-ray analysis apparatus of claim 7, further comprising an irradiation chamber formed above the sample and encompassing said portion of said X-ray guide member and said reflective surface.

10. The X-ray analysis apparatus of claim 7, wherein said X-ray guide member comprises an anti-reflection coating.

11. The X-ray analysis apparatus of claim 7, further comprising a collective lens between said reflective surface and said optical light receiving apparatus.

12. The X-ray analysis apparatus of claim 11, wherein said collective lens has a numerical aperture value greater than about 0.1.

13. The X-ray analysis apparatus of claim 7, wherein said X-ray guide member comprises a collimator.

14. The X-ray analysis apparatus of claim 13, wherein said collimator comprises a double-pinhole collimator cylinder.

15. The X-ray analysis apparatus of claim 7, wherein said reflective surface comprises a plurality of reflecting members.

16. The X-ray analysis apparatus of claim 7, wherein said reflective surface comprises a curved surface configured to focus said optical light onto said optical light receiving apparatus.

17. The X-ray analysis apparatus of claim 7, wherein said optical light receiving apparatus comprises an optical fiber.

18. The X-ray analysis apparatus of claim 7, wherein said optical light receiving apparatus comprises a CCD camera.

19. The X-ray analysis apparatus of claim 7, further comprising a mirror proximate said portion of said X-ray guide member and between the sample and said reflective surface, said mirror configured to receive light from the sample and reflect the light as a parallel beam onto said reflective surface.

20. The X-ray analysis apparatus of claim 7, wherein said X-ray guide member comprises an X-ray guide tube.

21. An X-ray analysis apparatus for irradiating a sample with X-rays and providing a visual image of the sample comprising:
   an X-ray guide member for transmitting X-rays to the sample along an elongated conduit;
   a reflective surface having one of a shallow cut portion extending inward from a perimeter of the reflective surface and a deep cut portion extending inward from a perimeter of the reflective surface, the respective cut portions are configured to extend on either side of the elongated conduit of the X-ray guide member as it protrudes from the reflective surface, the reflective surface reflects light forming an image of the sample; and
   an optical light receiving apparatus for receiving reflected light from the reflective surface and forming an image of the sample.

22. An X-ray analysis apparatus comprising:
   an X-ray guide member for transmitting X-rays to a surface of the sample such that said sample is directly irradiated with the X-rays along a first path; and
   an optical reflective surface for receiving light reflected from said surface along a second path having a perimeter with an inwardly extending cut portion with the X-ray guide member extending through the cut portion and beyond the reflective surface,
   wherein said first path and said second path are substantially coaxial.

23. An X-ray analysis apparatus for irradiating a sample with X-rays and visible light comprising:
   a source of X-rays;
   an elongated X-ray guide member having at least a progressively narrower conduit with an exit portion to emit a narrow X-ray beam operatively connected to the source of the X-rays;
   a sample stage for positioning a sample;
   an X-ray detector operatively positioned to detect an interaction of the X-rays and a sample on the sample stage;
   a visible light reflector with a reflective surface for imaging a sample on the sample stage having a portion for receiving an intermediate portion of the elongated X-ray guide member with the X-ray guide member exit portion spaced from the reflective surface adjacent the sample stage; and
   a visible light image detector for receiving an image of the sample.

24. The X-ray analysis apparatus according to claim 23 wherein the X-ray guide member exit portion is spaced to block stray visible light while providing a clear field of view for the X-ray detector.

* * * * *